US00PP16715P3

(12) United States Plant Patent

Anderson, III et al.

(10) Patent No.: US PP16,715 P3

(45) Date of Patent: Jun. 27, 2006

(54) *PISTACHIO* ROOTSTOCK TREE NAMED 'P.N. 20-18'

(50) Latin Name: ***Pistacia* sp.**
Varietal Denomination: P.N. 20-18

(76) Inventors: Henry P. Anderson, III, 3740 West Caldwell Ave., Visalia, CA (US) 93277; Kenneth L. Puryear, 5911 West Prospect Dr., Visalia, CA (US) 93291

( * ) Notice: Subject to any disclaimer, the term of this patent is extended or adjusted under 35 U.S.C. 154(b) by 112 days.

(21) Appl. No.: 10/807,642

(22) Filed: Mar. 23, 2004

(65) Prior Publication Data

US 2005/0216981 P1 Sep. 29, 2005

(51) Int. Cl.
*A01H 5/00* (2006.01)

(52) U.S. Cl. ..... Plt./152

(58) Field of Classification Search ..... Plt./152
See application file for complete search history.

(56) References Cited

U.S. PATENT DOCUMENTS

| | | | | |
|---|---|---|---|---|
| PP4,953 P | | 11/1982 | Anderson et al. | |
| PP4,994 P | | 3/1983 | Anderson et al. | |
| PP10,274 P | * | 3/1998 | Nevo | Plt./152 |
| PP10,275 P | * | 3/1998 | Nevo | Plt./152 |
| PP14,132 P2 | | 9/2003 | Anderson et al. | |
| PP14,706 P2 | | 4/2004 | Anderson et al. | |

OTHER PUBLICATIONS

Huxley, et al. 1992, "The New Royal Horticultural Society Dictionary of Gardening", vol. 3, The MacMillan Press Limited, London, The Stockton Press, New York, pp. 596–597.*

* cited by examiner

*Primary Examiner*—Howard J. Locker
(74) *Attorney, Agent, or Firm*—Christie, Parker & Hale, LLP

(57) ABSTRACT

A new and distinct variety of *pistachio* tree, characterized by the rounded and upright growth of the plant and the glabrous and leathery characteristic of the foliage, which is particularly useful as a rootstock upon which commercial nut bearing *pistachio* varieties may be budded or grafted.

4 Drawing Sheets

Latin name of genus and species: The present invention relates to a new *Pistacia* sp. tree, designated 'P.N. 20-18'.

BACKGROUND OF THE INVENTION

The present invention relates to a new and distinct variety of *pistachio* tree. The new variety was discovered in an open-pollinated seed plot in Delano, Calif. Seeds were collected from the seed plot in 1988 and planted in 1989 for testing. Yield data was collected from 1998 to 2000.

SUMMARY OF THE INVENTION

The 'P.N. 20-18' variety is characterized by the rounded and upright growth of the plant, the glabrous and leathery characteristic of the foliage, and its particular usefulness as a rootstock upon which commercial nut bearing *pistachio* varieties may be budded or grafted. Testing of the new variety as a rootstock revealed that stock grafted onto the new variety produce more fruit than stock grafted onto *P. integerrima*. The parents of the 'P.N. 20-18' variety are unknown.

'P.N. 20-18' was used as a rootstock for Kerman *pistachios* and shown to produce a superior yield of fruit. Cuts were made to this 'P.N. 20-18' rootstock to generate suckers, which were budded onto *P. integerrima* to produce bud wood. Tissue culture was used to propagate more rootstock. Asexual reproduction by budding onto *P. integerrima* at Kern County, Calif. and by tissue culture show that the foregoing and other distinguishing characteristics come true to form and are established and transmitted through succeeding propagation. Other known forms of asexual reproduction for *pistachios* may also be employed.

BRIEF DESCRIPTION OF ILLUSTRATIONS

The accompanying photographic illustrations show typical specimens of vegetative growth of the new variety, in color as nearly true as it is reasonably possible to make in a color illustration of this character.

DESCRIPTION OF THE NEW VARIETY

Referring now specifically to the new and distinct variety of *pistachio* tree, the following is a detailed description of one year old trees (grafted onto three year old *P. integerrima* rootstock) with color description where indicated by reference to The Royal Horticultural Society Colour Chart, except where common terms of color definition are employed.

The new variety of *pistachio* tree as herein described may vary in slight detail due to climatic, soil and cultural conditions under which the variety may be grown, the present description being of the variety as grown at McFarland, Kern County, Calif.

Figure 1:
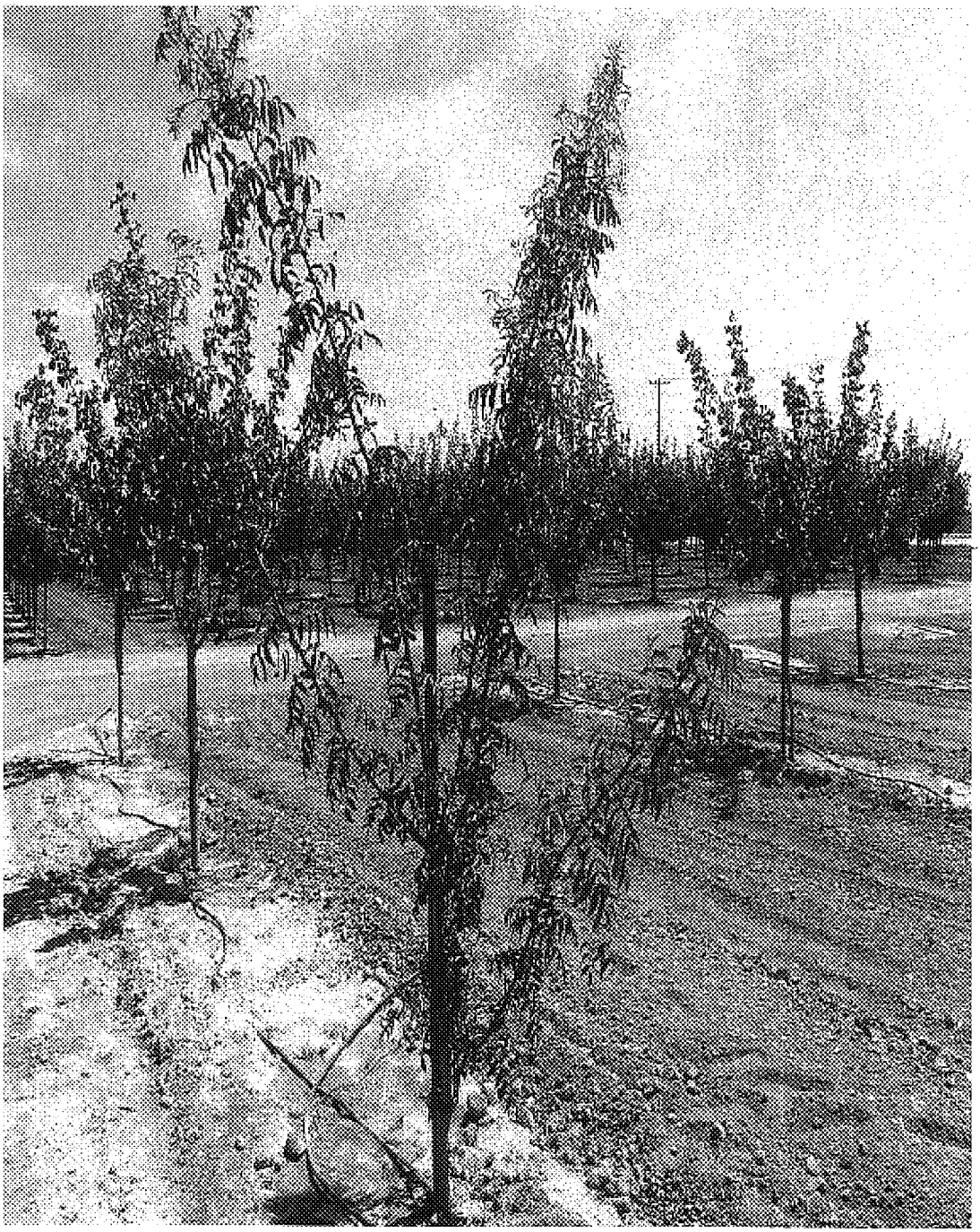
FIG. 1 shows a three year old *pistachio* tree of the new variety.

Plant:

*Growth.*—Rounded and upright, as indicated in FIG. 1.

Figure 2:
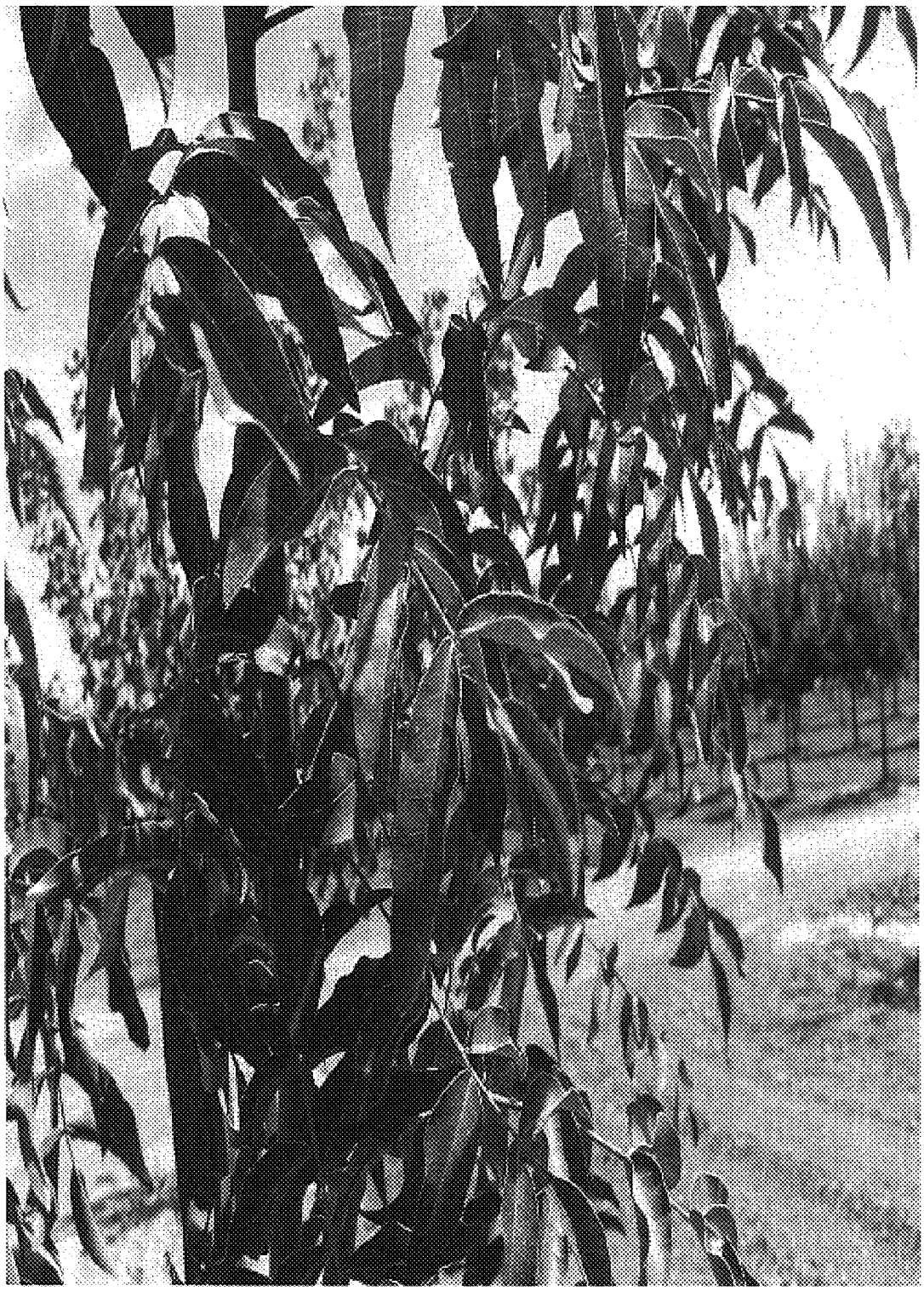
FIG. 2 shows a close-up of the compound leaves, typically with thirteen leaflets.

Foliage:

*Leaves.*—Compound of thirteen leaflets (sometimes less), as indicated in FIG. 2. Length and Width — Approximately 8 inches long and 5 inches wide at the widest point.

Figure 3:
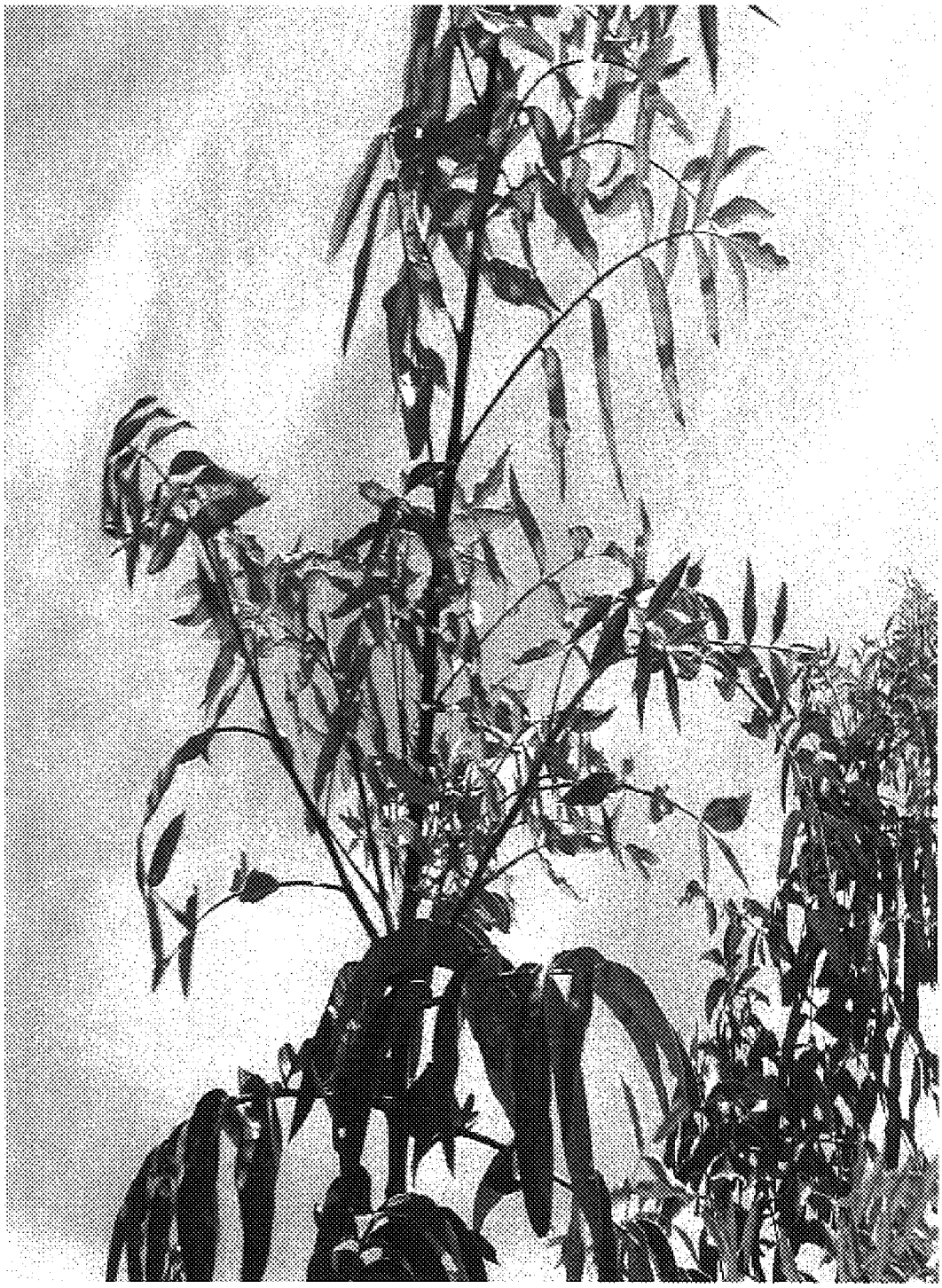
FIG. 3 shows a close-up of the new variety with both medium red to reddish green new leaflets and dark green older leaflets.

*Leaflets.*—Small, with young tissue glossy and lighter green than older tissue, which is dull and darker green. Shape — Medium length and lanceolate, apex acute, base cuneate. Color — New leaflets are medium red to a reddish green, near Greyed-red Group 178B (top surface) and 178B–C (bottom surface), as shown in FIG. 3. Older leaflets are dark green, near Yellow-green Group 147A (top surface) and 147 B (bottom surface), also as shown in FIG. 3. Arrangement — Pinnately compound of thirteen, sometimes less, nearly opposite, lanceolate and sessile. Margin, Venation pattern and color, length (without petiole), width, and texture — Entire with a pinnate and alternate venation pattern; veins are light green, near 147C (mature foliage) or 194C (young foliage). Apex of leaflets is acute. Base of leaf cuneate. The length of the leaflet averages 2.43 inches and 0.82 inches wide at widest spot. The leaflet has a leathery characteristic on top with a smoother surface on bottom. Leaf surface is glabrous. Leaflet Ribs — Ribs of leaflets are green (near 147C in mature leaflets and near 194C in young leaflets).

*Rachis length and color.*—Rachis length is about 4.41 inches; rachis color is greyed-green, near 195C, with a reddish color, near 181C, at the base. Rachis color on young leaves is greyed-red, near 181A–181C.

*Petiole length, diameter, and color.*—Petiole length is about 1.43 inches, with a diameter of about 0.102 inches; petiole color is greyed-purple, near 182B.

Growth:

*Height.*—About 8 feet.

*Spread.*—About 4 feet.

*Trunk.*—Trunk is rounded.

Figure 4:
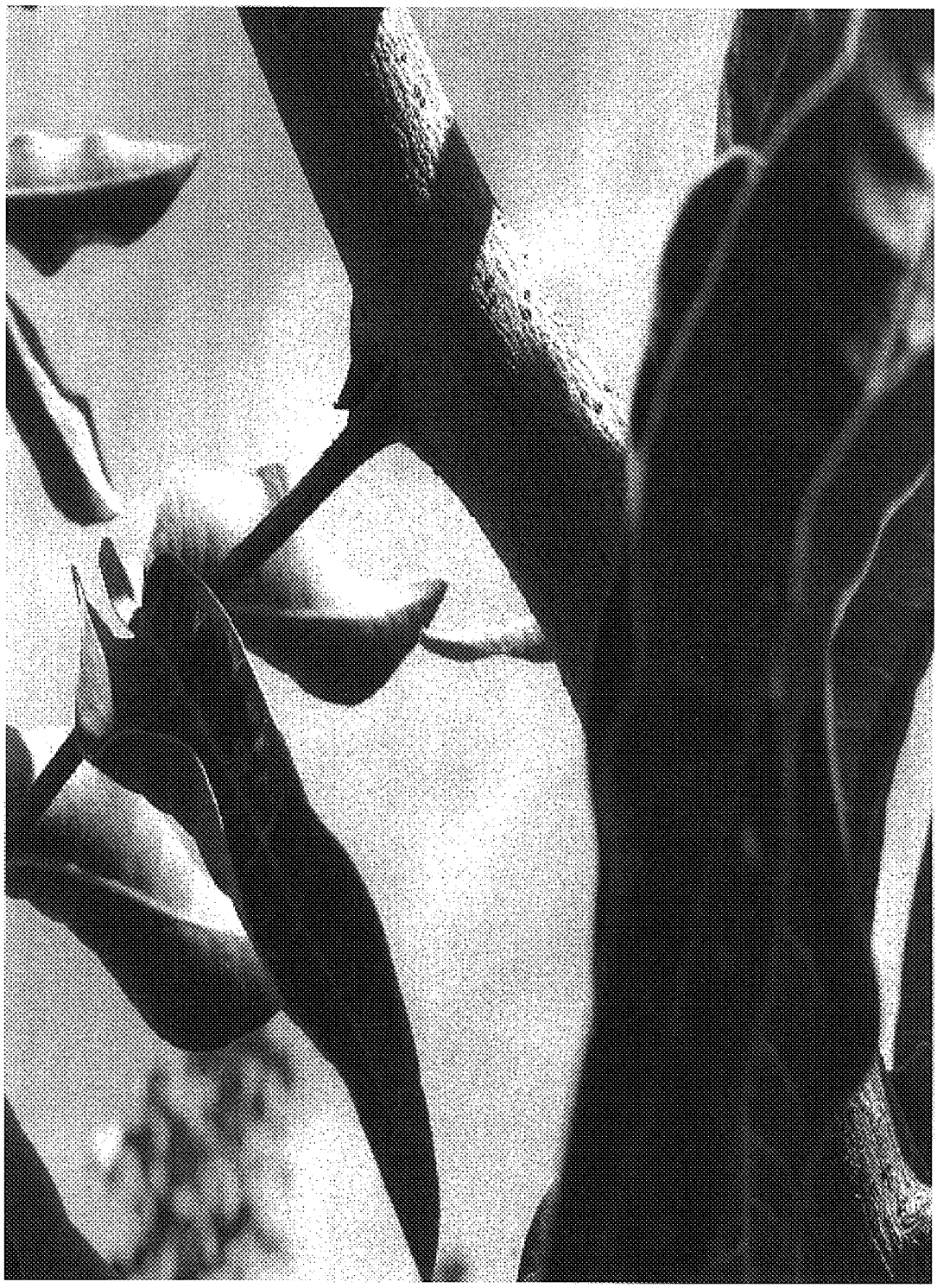
FIG. 4 shows a close-up of the trunk of the new variety.

*Trunk color.*—The trunk is light brown in color, near Greyed-orange Group 165A, on older growth and red, near Greyed-red Group 178B, in newer growth, as shown in FIG. 4.

*Trunk diameter.*—About 1.58 inches at 12 inches above soil surface.

*Bark texture.*—Rough.

*Vegetative buds.*—Vegetative buds are small and reddish on new growth and green and larger on older growth.

We claim:

1. A new and distinct variety of *pistachio* tree, identified as 'P.N. 20-18', substantially as shown and described.

* * * * *